US00PP08939P

United States Patent [19]

Atchison

[11] Patent Number: Plant 8,939

[45] Date of Patent: Oct. 11, 1994

[54] *FICUS BENJAMINA* CV. 'TOOLITTLE'

[76] Inventor: James K. Atchison, 1247 Gondola Ct., Boyton Beach, Fla. 33426

[21] Appl. No.: 156,290

[22] Filed: Nov. 19, 1993

[51] Int. Cl.[5] ..... A01H 5/00
[52] U.S. Cl. ..... Plt./88.9
[58] Field of Search ..... Plt. 88.9

*Primary Examiner*—James R. Feyrer
*Attorney, Agent, or Firm*—Synnestvedt & Lechner

[57] ABSTRACT

A new and distinct variety of *Ficus benjamina* plant named 'TooLittle' which is particularly characterized by its unique, small leaves which curl downward, its very tight internode space, and its dense and extremely slow growth habit.

7 Drawing Sheets

BACKGROUND AND SUMMARY OF THE INVENTION

This invention relates to the discovery and asexual propagation of a new variety of a *Ficus benjamina* plant that has been named 'TooLittle.'

'TooLittle' is a chance mutant of *Ficus benjamina* that was discovered in April of 1988 by James K. Atchison, growing in a cultivated planting of *Ficus benjamina* plants at Parrish Tropicals, Inc., a nursery in Delray Beach, Fla. Cuttings from the mutant plant were taken by James K. Atchison, and they were asexually reproduced at the nursery in May of 1988 under the direction and supervision of James K. Atchison. It was subsequently found that the plants which were replicated asexually from the original cuttings, and also in succeeding propagations made over ten generations from cuttings, held the distinguishing characteristics of 'TooLittle.'

'TooLittle' can be distinguished from the parent, *Ficus benjamina* by its unique, small curled leaves, very tight internode space, and dense and extremely slow growth. 'TooLittle' is a very full plant, whereas the parent *Ficus benjamina* is less dense in nature.

The 'TooLittle' plant has leaves approximately 7 to 10 times more in quantity than that of the parent *Ficus benjamina* variety. The 'TooLittle' leaves are approximately $\frac{1}{4}$ to $\frac{1}{3}$ the size of the parent *Ficus benjamina* leaf, and curl downward slightly. The numerous quantity of leaves gives this plant its dense appearance. The plant can be pruned to tree form and it can also be grown as a shrub. The small size and the extremely slow growth of the *Ficus benjamina* 'TooLittle' make it an excellent candidate for the Bonsai market.

The branching of the *Ficus benjamina* 'TooLittle' differs both in that it branches without pruning (from each node), and has extremely tight internode space compared to that of the parent *Ficus benjamina*. Branching of the 'TooLittle' plant is numerous, expansive, upright and spreading. Branching of the parent *Ficus benjamina* plant is much more sparse and has a weeping appearance.

The bark of 'TooLittle' is light green with new growth, and a gray-brown with old growth, which is similar to that of the parent *Ficus benjamina*. Small and medium aerial roots form near the base of the plant, as is common with many Ficus varieties. Very large, yet sparse, roots form under the soil level. These roots can be exposed to add to a Bonsai effect.

BRIEF DESCRIPTION OF THE FIGURES

The accompanying drawings illustrate the new *Ficus benjamina* 'TooLittle' as grown under full sun. Plants grown under shade exhibit larger leaves and internode space, darker green foliage and slightly quicker, upright growth. All plants were grown in a soil mix compound of 50 percent Canadian peat, 30 percent composted pine bark, 20 percent cypress chips and 10 percent sand. The soil was incorporated with Nutricoat 18-6-8 as nutrient levels fell off. The plants were top-dressed with Nurserymans Sure Grow 17-4-11.

BOTANICAL DESCRIPTION OF THE PLANT

Figure 1:
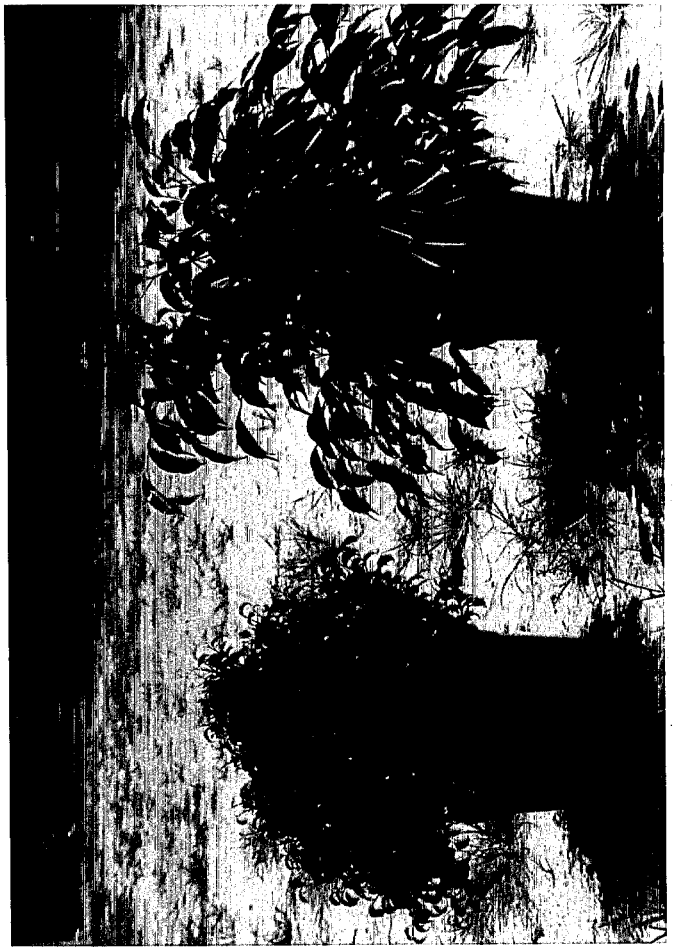
FIG. 1 in the accompanying drawings illustrates the parent *Ficus benjamina* variety (6 to 8 months old) and the new *Ficus benjamina* 'TooLittle' (18 months old) varieties in a side-by-side comparison, with *Ficus benjamina* 'TooLittle' on the left and the parent *Ficus benjamina* variety on the right.
Figure 2A:
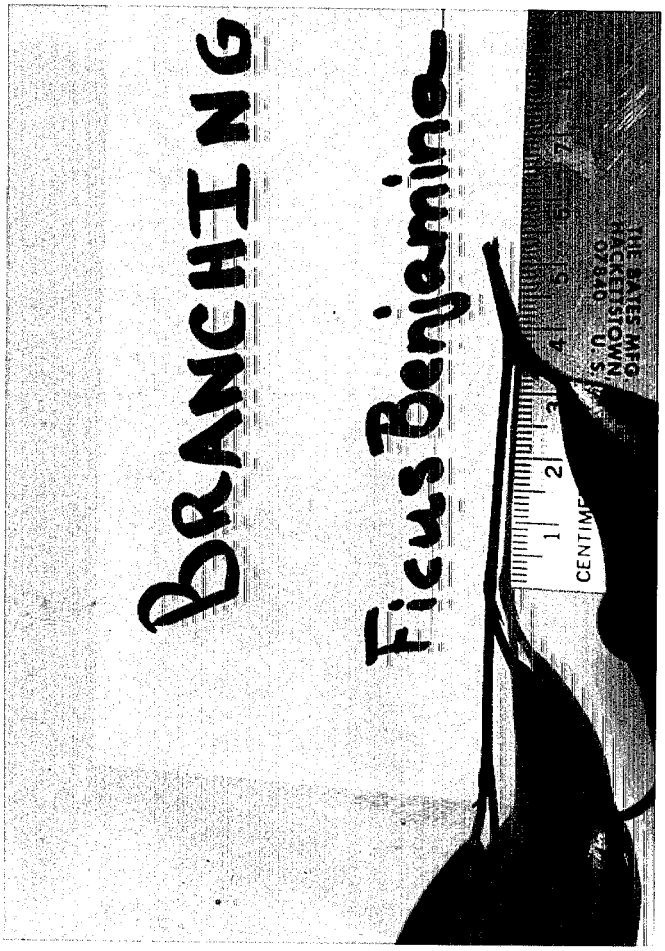
*FIGS. 2–A and 2–B in the accompanying drawings illustrate, respectively, the branching of the parent Ficus benjamina* variety and the *Ficus benjamina* 'TooLittle,' with FIG. 2–C illustrating a side-by-side comparison of the two varieties. The drawings particularly illustrate the tight internode space and branching at each node characteristic of the new 'TooLittle' variety.
Figure 2B:
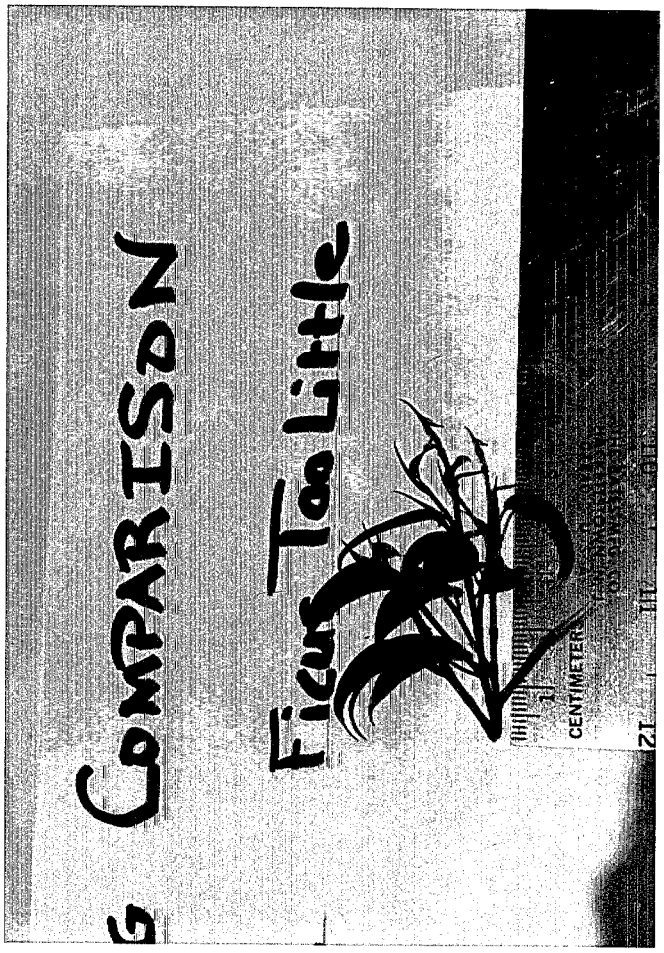
Figure 2C:
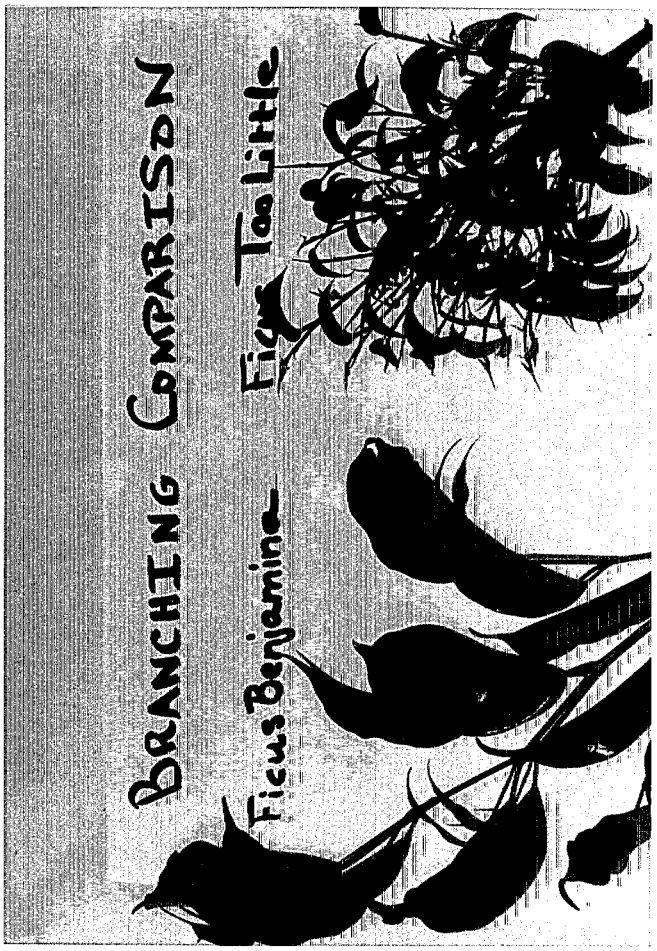
Figure 3A:
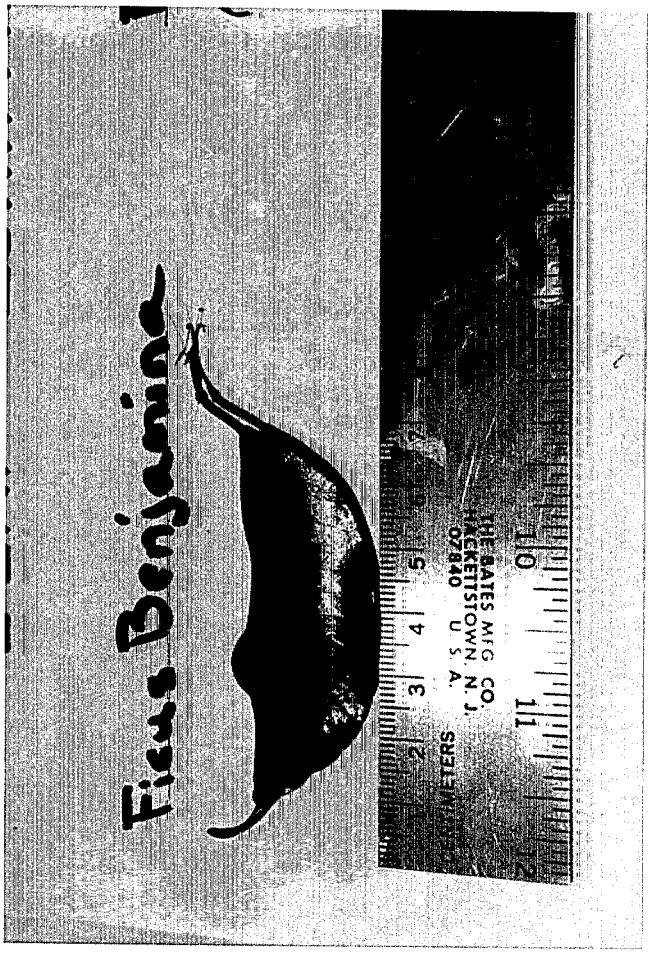
FIGS. 3–A and 3–B in the accompanying drawings illustrate, respectively, the leaf charcteristics of the parent *Ficus benjamina* and the *Ficus benjamina* 'TooLittle,' with FIG. 3–C illustrating a side-by-side comparison of the leaves. Both leaves illustrated are fully mature. The drawings particularly illustrate the small, curled leaves of the new 'TooLittle' variety.
Figure 3B:
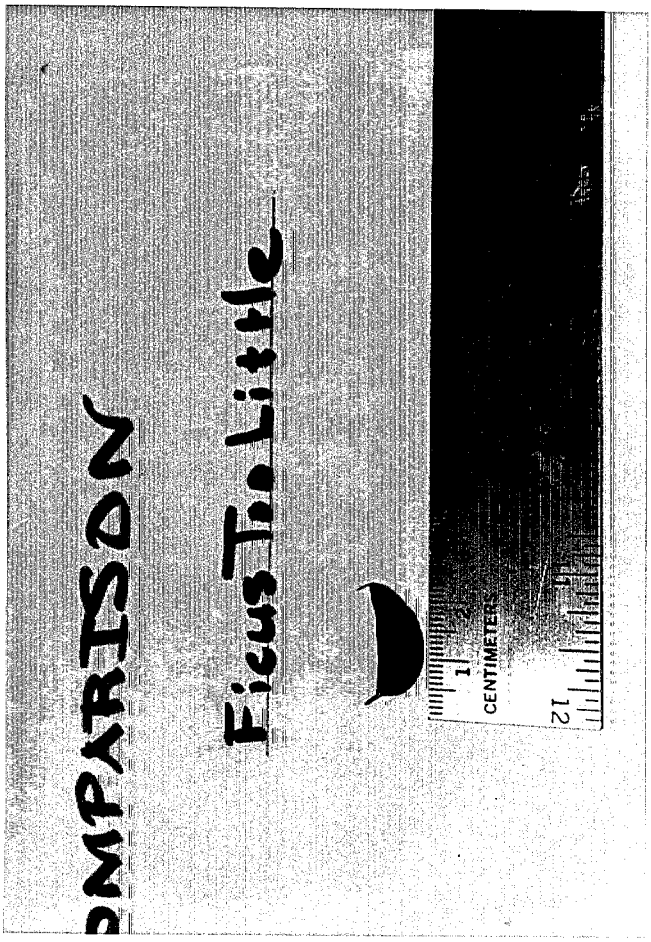
Figure 3C:
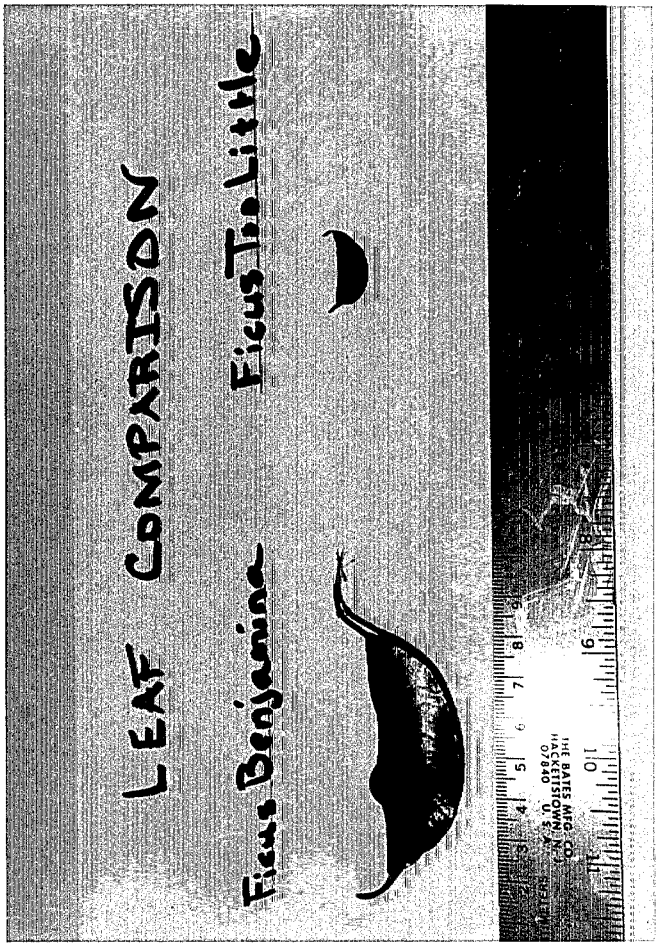

Throughout this specification, color names beginning with a small letter signify that the name of that color as used in common speech is aptly descriptive. Color names beginning with a capital letter designate color values based on The R.H.S. Colour Chart published by The Royal Horticultural Society of London, England.

The descriptive matter which follows pertains to *Ficus benjamina* 'TooLittle' plants grown in the vicinity of Delray Beach, Fla., and is believed to apply to plants of the variety grown under similar conditions of soil and climate elsewhere.

The Plant

General characteristics: The plant is generally an upright, spreading, and compact shrub, which demonstrates extremely slow growth. It is generally smaller than the parent *Ficus benjamina*, with less vigor. One year old plants are about 12 to 14 inches in height and about 8 to 10 inches in width.

Branches: The plant has a large quantity of ascending branches. Immature branches are a light green and mature, older branches are a gray-brown in color. A central branch or trunk is formed when pruned; otherwise 'TooLittle' branches from the base of the plant. 'TooLittle' can be pruned as a tree or a shrub. The caliper of the central branch at the base of a one year old plant is average, i.e., about $1\frac{1}{2}$ to 2 cm. in diameter. Internodes are closely spaced, approximately 1 cm. apart.

Foliage

Amount: The quantity of foliage is relatively heavy (about 7 to 10 times that of the parent *Ficus benjamina*) and compact.

Size: Mature leaves are about $\frac{1}{4}$ to $\frac{1}{3}$ the size of those of the parent *Ficus benjamina*. Mature 'TooLittle' leaves are between about $1\frac{1}{2}$ to 2 cm. long and about $\frac{3}{4}$ to 1 cm. wide, 1 cm. being the average width. The petiole is about $\frac{1}{2}$ cm. long.

Color: The upper leaf surface in mature foliage is dark green and glossy; the lower leaf surface is paler and somewhat duller.

Shape: The leaves are alternate in arrangement and ovate in form. The leaf apex is caudate in shape and curled downward; the base is V-shaped. Leaf margins are entire and there is no undulation. 'TooLittle' leaves can be distinguished from those of the parent *Ficus benjamina*, in that they are smaller and curl downward.

Venation: The veins are very fine and pinnate in arrangement. They are barely raised above the surface. Secondary veins attach to the superadjacent vein and are in similar concentration near the leaf margins. The midrib is prominent.

Shoot tip: The shoot tip is about $\frac{3}{4}$ to 1 cm. long and light green in color.

Texture: The foliage is smooth in texture when mature.

Fruit

Fruits have not been observed.

I claim:

1. A new and distinct variety of *Ficus benjamina* plant named 'TooLittle' as herein illustrated and described.

* * * * *